(12) United States Patent
Bencini et al.

(10) Patent No.: US 6,666,864 B2
(45) Date of Patent: Dec. 23, 2003

(54) ELECTROPHYSIOLOGICAL PROBES HAVING SELECTIVE ELEMENT ACTUATION AND VARIABLE LESION LENGTH CAPABILITY

(75) Inventors: Robert F. Bencini, Sunnyvale, CA (US); Miriam H. Taimisto, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 90 days.

(21) Appl. No.: 09/896,131

(22) Filed: Jun. 29, 2001

(65) Prior Publication Data

US 2003/0004505 A1 Jan. 2, 2003

(51) Int. Cl.[7] .......................... A61B 5/042; A61B 18/14
(52) U.S. Cl. .......................... 606/41; 600/374; 600/381; 607/122
(58) Field of Search ................................ 600/374, 381; 606/41; 607/122

(56) References Cited

U.S. PATENT DOCUMENTS

| | | | | |
|---|---|---|---|---|
| 4,476,872 A | * | 10/1984 | Perlin | 600/380 |
| 4,483,574 A | * | 11/1984 | Chabrerie et al. | 439/5 |
| 4,744,370 A | * | 5/1988 | Harris | 607/122 |
| 5,607,422 A | * | 3/1997 | Smeets et al. | 606/41 |
| 5,824,030 A | * | 10/1998 | Yang et al. | 607/122 |
| 5,826,576 A | * | 10/1998 | West | 607/122 |
| 6,017,338 A | * | 1/2000 | Brucker et al. | 606/41 |
| 6,238,390 B1 | | 5/2001 | Tu et al. | |
| 6,241,727 B1 | | 6/2001 | Tu et al. | |
| 2002/0099428 A1 | * | 7/2002 | Kaufman | 606/41 |

* cited by examiner

*Primary Examiner*—Lee Cohen
(74) *Attorney, Agent, or Firm*—Henricks, Slavin & Holmes LLP

(57) ABSTRACT

An apparatus having a support structure, a plurality of longitudinally spaced conductive regions, and an actuation device including at least one electrical contact located within the support structure and movable between respective positions where the one electrical contact is in electrical connection with one of the spaced conductive regions.

22 Claims, 11 Drawing Sheets

ELECTROPHYSIOLOGICAL PROBES HAVING SELECTIVE ELEMENT ACTUATION AND VARIABLE LESION LENGTH CAPABILITY

BACKGROUND OF THE INVENTIONS

1. Field of Inventions

The present inventions relate generally to medical devices that support one or more diagnostic or therapeutic elements in contact with body tissue.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and flexible body portion that supports a soft tissue coagulation electrode on its distal end and/or a series of spaced soft tissue coagulation electrodes near the distal end. The portion of the catheter body that is inserted into the patient is typically from 23 to 55 inches in length and there may be another 8 to 15 inches, including a handle having steering controls, outside the patient. The length and flexibility of the catheter body allow the catheter to be inserted into a main vein or artery (typically the femoral artery), directed into the interior of the heart, and then manipulated such that the coagulation electrodes contact the tissue that is to be ablated. Fluoroscopic imaging is used to provide the physician with a visual indication of the location of the catheter.

Therapeutic lesions, whether formed alone or as part of a therapeutic lesion pattern, must often be formed in varying lengths to suit particular situations. In those instances where the catheter includes a single tip electrode, the physician must manipulate the catheter so that the tip electrode is dragged along the desired length of tissue during lesion formation. Such a technique is problematic because it is difficult to properly execute and often results in incomplete lesions, lesion gaps and tissue charring. Superior results have been obtained using catheters that support multiple electrodes. Here, some or all of the electrodes on the catheter may be selectively connected to an energy source to produce lesions of various lengths. The inventors herein have determined that, while superior to the drag technique, forming lesions of various lengths with conventional multiple electrode catheters can be inconvenient because such catheters require the use of a power supply and control device that is capable of selectively connecting some or all of the electrodes to the energy source.

SUMMARY OF THE INVENTION

An apparatus in accordance with one embodiment of one present invention includes a support structure, a plurality of longitudinally spaced conductive regions, and an actuation device including at least one electrical contact located within the support structure and movable between respective positions where the electrical contact is in electrical connection with a respective conductive region.

Such an apparatus provides a number of advantages over conventional apparatus. For example, lesions of various lengths and configurations may be produced by forming a portion of an overall lesion when the actuation device is in one position, then moving the actuation device to another position to form an additional portion of the lesion, and so on until the desired lesion is formed. As a result, the apparatus allows physicians to selectively actuate some or all of the conductive regions to form a variety of lesions without having to use a power supply and control device that is itself capable of selectively connecting some or all of the conductive regions to an energy source. Additionally, because such an apparatus also allows lesions of varying length to be created without moving the support structure, the precise positioning of the apparatus will not be compromised and the unintended ablation of non-target tissue will be prevented.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
I. Introduction
II. Catheter-Based Probe Structures
III. Catheter-Based Probe Structures With Porous Distal Regions
IV. Imaging
V. Surgical Probe Structures
VI. Temperature Sensing and Power Control The section titles and overall organization of the present detailed description are for the purpose of convenience only and are not intended to limit the present inventions.

I. Introduction

The present inventions may be used within body lumens, chambers or cavities for diagnostic or therapeutic purposes in those instances where access to interior bodily regions is obtained through, for example, the vascular system or alimentary canal and/or with minimally invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, the distal portion of a probe in accordance with a present invention can be used to create lesions of various shapes, lengths and widths to treat atrial fibrillation. The distal portion can also be used for sensing.

II. Catheter-Based Probe Structures

As illustrated for example in FIGS. 1–5, a catheter 10 in accordance with a preferred embodiment of a present invention includes a hollow, flexible catheter body 12 that is formed from two tubular parts, or members, both of which are non-conductive. The proximal member 14 is relatively long and is attached to a handle 16, while the distal member 18, which is relatively short, carries a plurality of spaced electrodes 20 that may be used for lesion formation, sensing, etc. The proximal member 14 is typically formed from a biocompatible thermoplastic material, such as a Pebax® material (polyether block emide) and stainless steel braid composite or a polyethylene and stainless steel braid composite, which has good torque transmission properties. An elongate guide coil 22 (FIG. 4) is provided within the proximal member 14. The distal member 18 is typically formed from a softer, more flexible biocompatible thermoplastic material such as unbraided Pebax® material, polyethylene, or polyurethane. The proximal and distal members, which are about 5 French to about 9 French in diameter, may be either bonded together with an overlapping thermal bond or adhesively bonded together end to end over a sleeve in what is referred to as a "butt bond."

Figure 1:
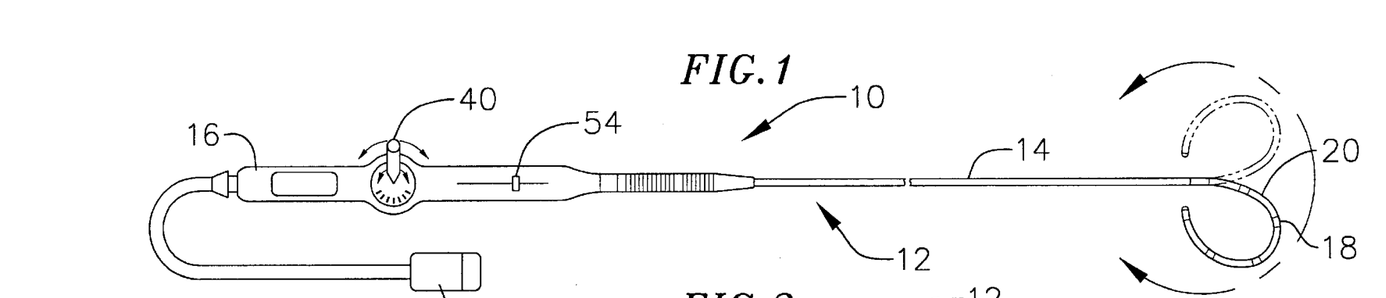
FIG. 1 is a side view of a probe in accordance with a preferred embodiment of a present invention.
Figure 2:
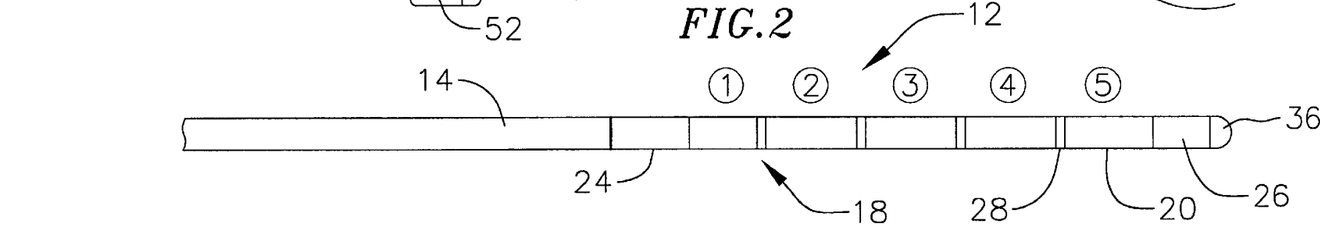
FIG. 2 is a side view of a portion of the probe illustrated in FIG. 1.
Figure 3:
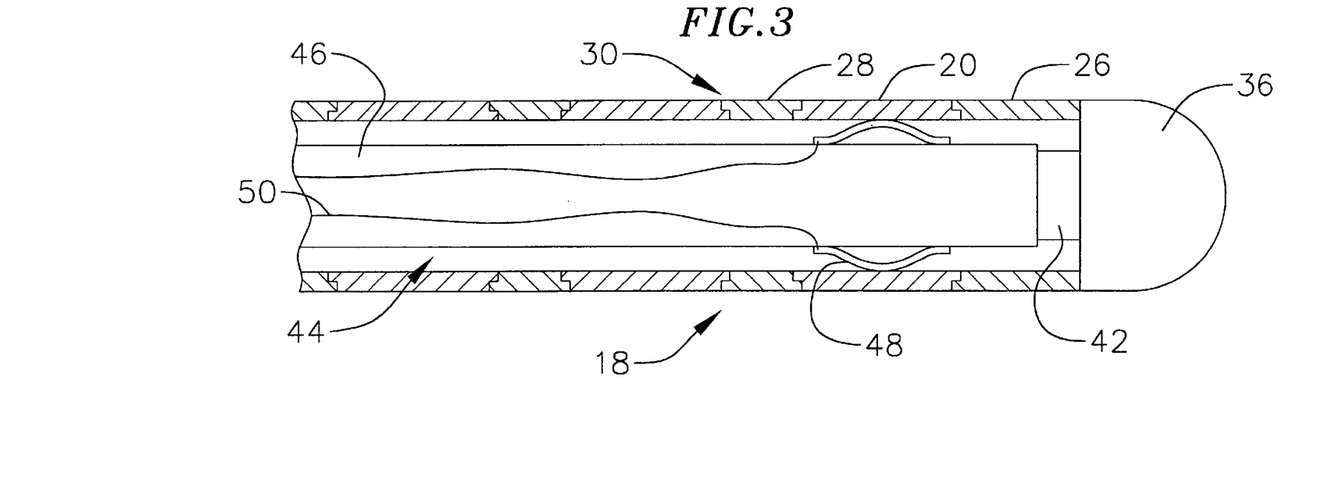
FIG. 3 is a side, partial section view of the distal portion of the probe illustrated in FIG. 1.

Referring more specifically to FIGS. 2 and 3, the exemplary distal member 18 includes a pair of end sections 24 and 26 and a plurality of intermediate sections 28 positioned between adjacent electrodes 20. Each of the sections 24–28 is non-conductive. The electrodes 20 may be secured to the distal member sections 24–28 with adhesive or thermal bonding techniques during assembly. In the exemplary embodiment, the lateral ends of the electrodes 20 and the distal member sections 24–28 have corresponding protrusions that together form lap joints 30. The exemplary embodiment illustrated in FIGS. 1–5 includes five (5) electrodes 20. Nevertheless, the number of electrodes 20 may be varied as desired to suit particular applications from as few as two (2) to as many as 14 or more.

The exemplary electrodes 20 may be formed from metal or a conductive plastic material. Suitable metals include platinum, while suitable conductive plastic materials include composites consisting of plastic and metal powder. The electrodes 20 may be in the form of rings, coiled wire or coil-cut tubing. Flexible electrodes are typically about 4 mm to about 13 mm in length, and are preferably about 12 mm in length with about 1 mm to about 4 mm spacing. For rigid electrodes, the length of the each electrode can vary from about 2 mm to about 10 mm with about 1 mm to about 4 mm spacing. Using multiple rigid electrodes longer than about 10 mm each adversely effects the overall flexibility of the device, while electrodes having lengths of less than about 2 mm do not consistently form the desired continuous lesion patterns.

In some implementations of the inventions, the portion of the electrodes 20 that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes 20 may also include a porous material coating, which transmits coagulation energy through an electrified ionic medium. For example, as disclosed in U.S. application Ser. No. 08/879,343, filed Jun. 20, 1997, entitled "Surface Coatings For Catheters, Direct Contacting Diagnostic and Therapeutic Devices," electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Finally, the electrodes 20 may be operated in a uni-polar mode, in which the soft tissue coagulation energy emitted by the electrodes is returned through an indifferent patch electrode (not shown) externally attached to the skin of the patient. Alternatively, the electrodes 20 may be operated in a bi-polar mode, in which energy emitted by one electrode is returned through a return electrode (not shown) that is mounted on the catheter.

The exemplary catheter 10 may also be steerable. To that end, and as illustrated for example in FIG. 4, a steering center support 32 is mounted on the distal end of the guide coil 22. The steering center support 32 is preferably about 0.035 inch wide, 0.005 inch thick, 2 to 6 inches long, and formed from stainless steel. Of course, center supports formed from other materials and having different dimensions may also be used. In order to increase the stiffness of the center support 32, optional leaf springs (not shown) may also be provided on one or both sides of the center support. The center support 32 includes a pair of shoulders 34. One of the shoulders is inserted into the guide coil 22 and the other is secured to a tip member 36 formed from platinum or another suitable material. The tip metal may be used as an electrode, if desired, or as a non-conducting atraumatic tip. Preferably, the shoulder 34 is soldered to the tip member 36 and the tip member is bonded to the distal member 18, thereby creating a rigid connection between the center support, the tip member, and the distal member.

Figures 4, 5:
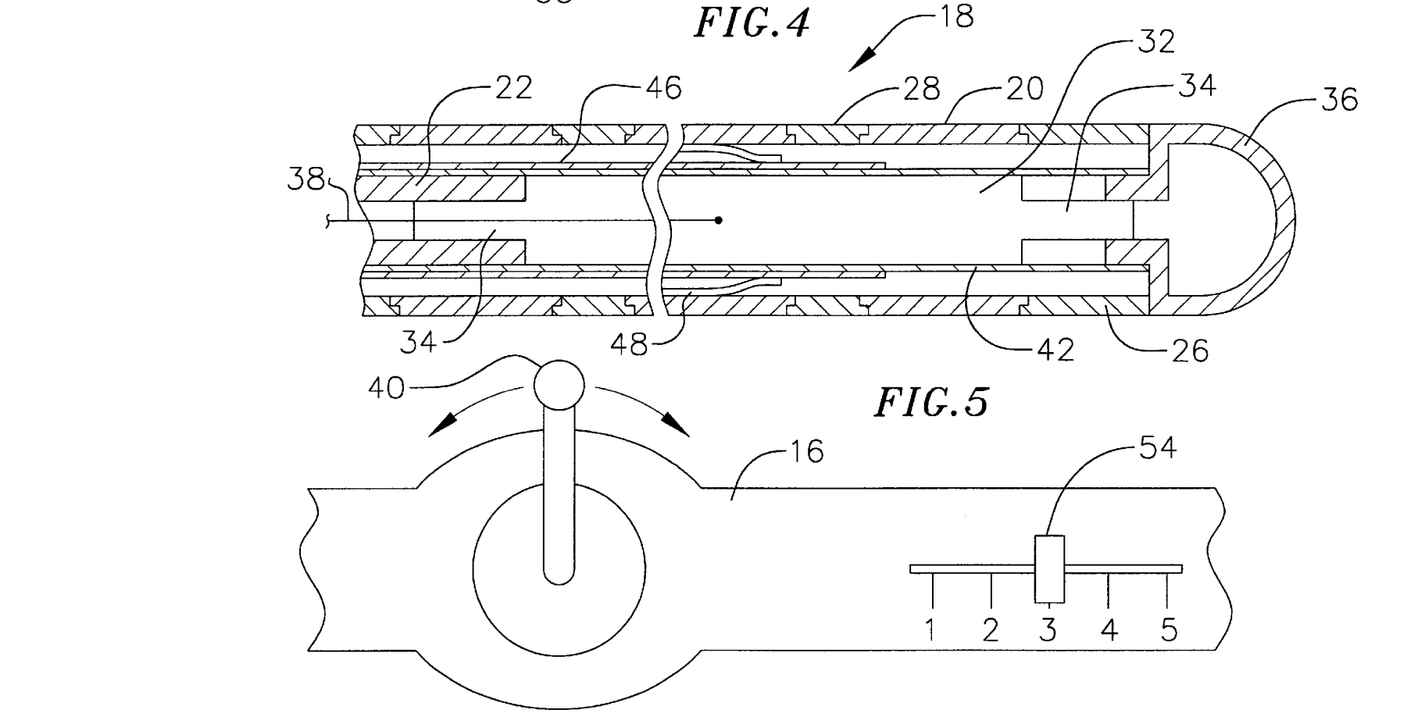
FIG. 4 is another side, partial section view of the distal portion of the probe illustrated in FIG. 1.
FIG. 5 is a side view of a portion of the handle in the probe illustrated in FIG. 1.

Steering wires 38 are secured to opposing sides of the steering center support 32. The steering wires 38 extend through the guide coil 22 and are connected to a control knob 40 on the catheter handle 16 (FIG. 5). Rotation of the control knob causes the center support 32 and, therefore, the distal portion of the catheter, to deflect. The guide coil 22, center support 32 and steering wires 38 are also preferably housed in an insulative tube 42 formed from material such as Kevlar, Teflon™ or polyester. Additionally, other types of steering devices, such as those discussed below with reference to FIGS. 11–20, may also be employed in the exemplary catheter 10.

Turning to the selective actuation of the electrodes 20 in the exemplary embodiment illustrated in FIGS. 1–5, i.e. the selective electrical connection of the electrodes to a device such as an RF power supply and control device or a mapping device, the exemplary catheter 10 is provided with a slidable actuator that allows the electrodes to be used individually as desired by the user. As illustrated for example in FIG. 3, the exemplary actuator 44 includes a tubular member 46 that is positioned over the insulative tube 42 and a pair of flexible spring-like electrical contacts 48 that are mounted on the tubular member and biased against the inner surface of the catheter body (or electrodes, depending on location). The number of electrical contacts may be varied to suit particular situations and taking into account factors such as impedance considerations in RF generator algorithms, but from one (1) to three (3) is preferred. Wires 50 extend from the electrical contacts 48 to a PC board in the handle 16 (FIG. 1), where they are electrically coupled to a connector 52 that plugs into the power supply and control or mapping device.

Figure 3A:
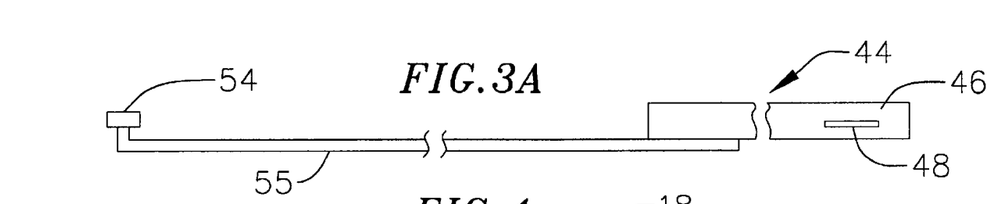
FIG. 3A is a side view showing a portion of the probe illustrated in FIG. 1.

The exemplary tubular member 46, which is preferably formed from nonconductive material such as Teflon, kynar, polyethylene, and polyamide and is about 50 inches in length, is connected to a slider 54 on the handle 16 by a stylet 55 (FIG. 3A). Alternatively, the tubular member 46 may simply extend all the way into the handle or be relatively short and have a length corresponding to that of the distal member 18 or less. Referring more specifically to FIGS. 2 and 5, the electrodes 20 are preferably numbered (1–5 in the illustrated embodiment) and corresponding indicia is provided on the handle 16 adjacent to the slider. The position of the slider 54 relative to the indicia on the handle 16 corresponds to the position of the electrical contacts 48 relative to the electrodes 20. Placing the slider 54 next to the "1" on the handle 16 will, for example, result in the tubular member 46 being positioned such that the electrical contacts 48 are in contact with electrode "1." Similarly, placing the slider next to the "2," "3," "4" and "5" respectively moves the electrical contacts 48 into contact with electrodes "2," "3," "4" and "5," respectively.

Additional details concerning catheter steering handles which include a control knob and a slider may be found in U.S. Pat. Nos. 5,257,451, 5,582,609, 5,871,523 and 5,928,191, which are incorporated herein by reference.

It should be noted that, in alternative embodiments, the actuator 44 (FIG. 3A) may include additional electrical contacts 48 positioned such that the actuator can make selective electrical connection with two or more adjacent or spaced electrodes to simultaneously actuate two or more adjacent electrodes, or two or more spaced electrodes.

Figure 6:
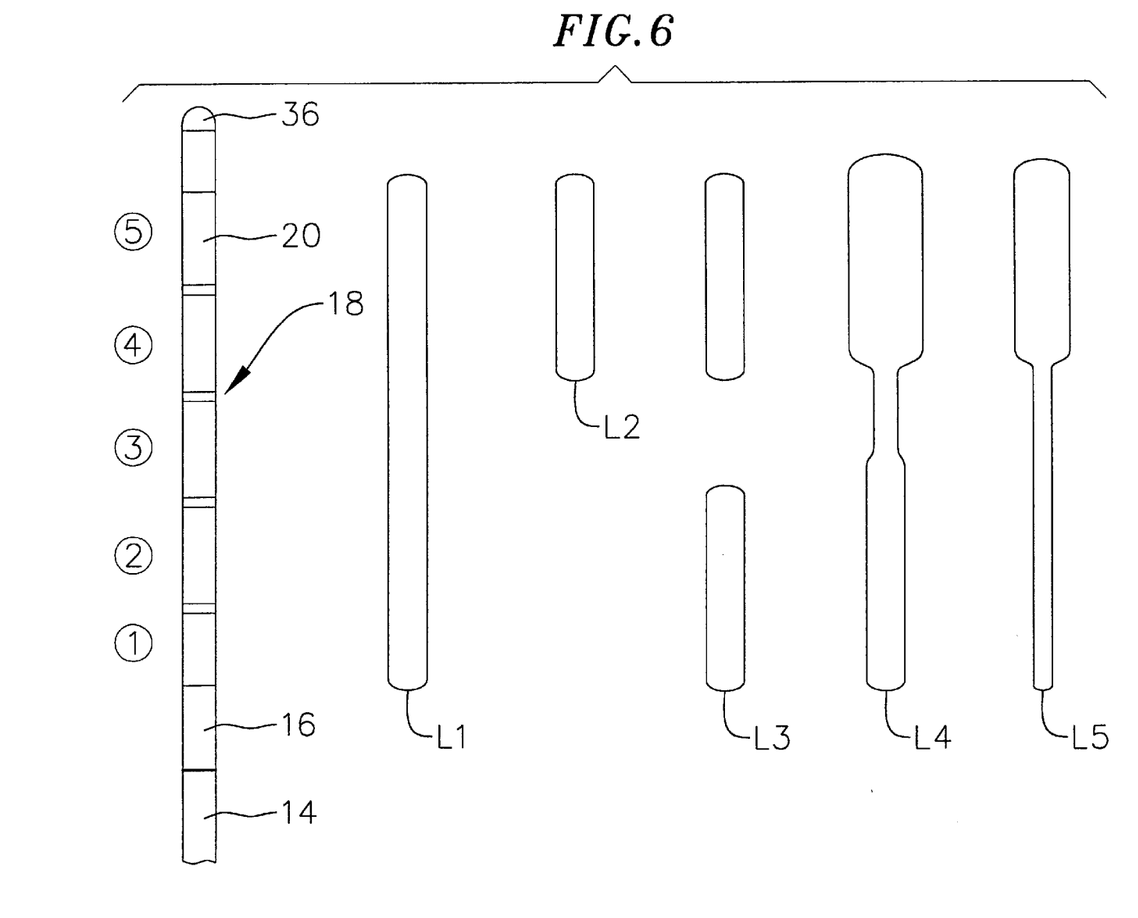
FIG. 6 is an illustration of exemplary lesions that may formed using probes in accordance with the present inventions.

Lesions of various lengths may be produced with the exemplary catheter 10 by forming a portion of an overall lesion when the actuator 44 is in one position, and then moving the actuator to another position to form additional portions of the lesion. Referring to FIG. 6, exemplary lesion L1 may be formed by first positioning the slider 54 at the "5" on the handle 16, thereby bringing the electrical contacts 48 into contact with electrode "5." Power is then supplied to electrode "5" by way of the electrical contacts 48 and wires 50. The slider 54 is then moved to the "4," "3," "2," and "1" positions, with power supplied to the corresponding electrode 20 at each position, to form a lesion that spans all five electrodes. Exemplary lesion L2, which is shorter than lesion L1, is formed by merely moving the slider 54 to the "5" and "4" positions and supplying power to electrodes "5" and "4," while lesion exemplary L3, which includes a gap, is formed by supplying power to electrodes "5," "4," "2" and "1."

The width of an entire lesion, or a portion of a lesion, may be varied by varying the amount of power, temperature set point, time applied, or some combination thereof. To produce exemplary lesion L4, a relatively large amount of power is supplied to electrodes "5" and "4" (about 50 watts for about 120 seconds), a relatively small amount of power is supplied to electrode "3" (about 20 watts for about 60 seconds) and an intermediate level of power (about 35 watts for about 120 seconds) is supplied to electrodes "2" and "1." It should be noted that the lesions may also be asymmetrical. Lesion L5, for example, is formed by supplying a relatively large amount of power to electrodes "5" and "4" and a relatively small amount of power to electrodes "3," "2" and "1." The same results may also be obtained by varying the temperature set point. For example, wide lesions may be produced with a 80° C. set point, while narrow lesions may be formed with a 65° C. set point. Curved lesions may also be formed by flexing the distal member 18 with the steering wires 38 during lesion formation.

Figures 7, 8:
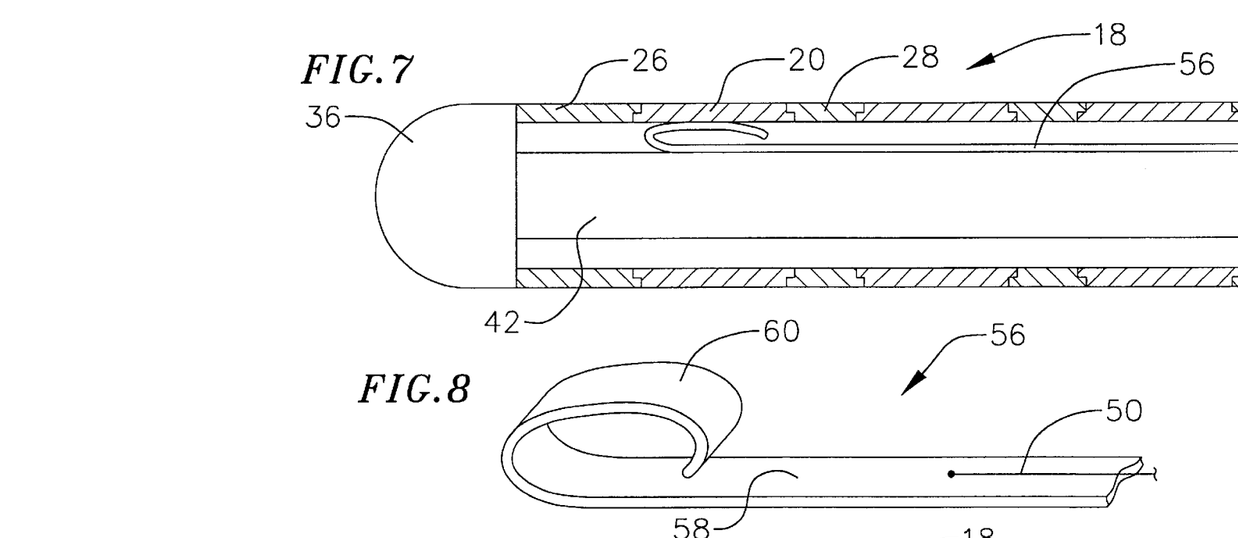
FIG. 7 is a side, partial section view of the distal portion of a probe in accordance with a preferred embodiment of a present invention.
FIG. 8 is a perspective view of the slidable actuator illustrated in FIG. 7.

The present inventions may be embodied in a variety of devices other than that illustrated in FIGS. 1–5. As illustrated for example in FIGS. 7 and 8, a slidable actuator 56 may be used in place of the slidable actuator 44 illustrated in FIGS. 3 and 4. The slidable actuator 56, which is connected to a wire 50 and is formed from flexible conductive material such as copper or 304 stainless steel, consists of a generally flat elongate portion 58 that slides along the insulative tube 42 and a curved, spring-like electrical contact 60 that maintains contact with the inner surface of the non-conductive portions of the distal member 18, or electrodes 20, depending on its position. The actuator 56 is also connected to the slider 54 by a stylet (not show). As such, the electrical contact 60 may be moved from electrode to electrode in the manner described above.

Figure 9:
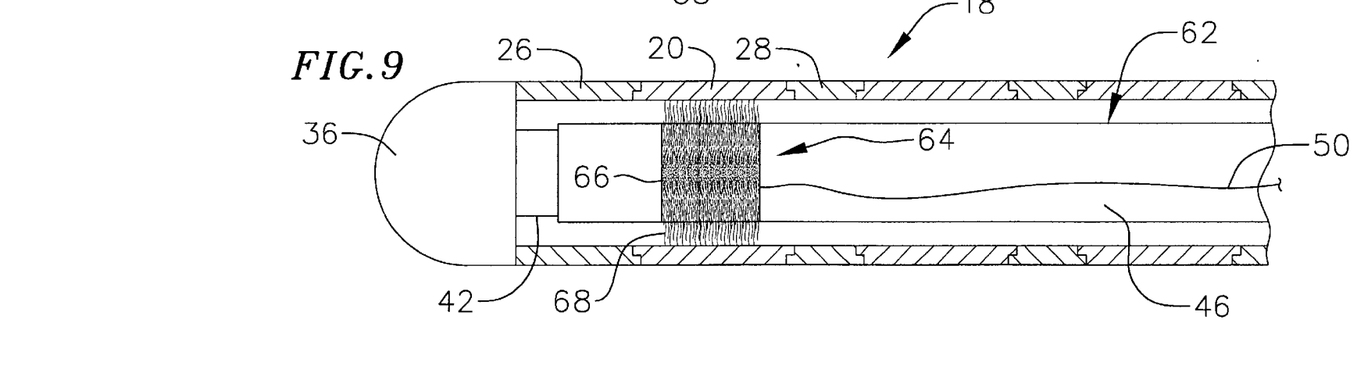
FIG. 9 is a side, partial section view of the distal portion of a probe in accordance with a preferred embodiment of a present invention.

Another slidable actuator, which is generally represented by reference numeral 62 in FIG. 9, includes an electrical contact brush 64 that is mounted on the tubular member 46 in place of the spring-like contacts 48. The brush 64 includes a conductive base 66 to which a wire 50 is connected and a plurality of conductive bristles 68 that engage the inner surface of the non-conductive portions of the distal member 18 and the electrodes 20. Here too, the tubular member 46 is connected to the slider 54 by a stylet and, accordingly, the electrical contact brush 64 may be moved from electrode to electrode in the manner described above.

Figure 10:
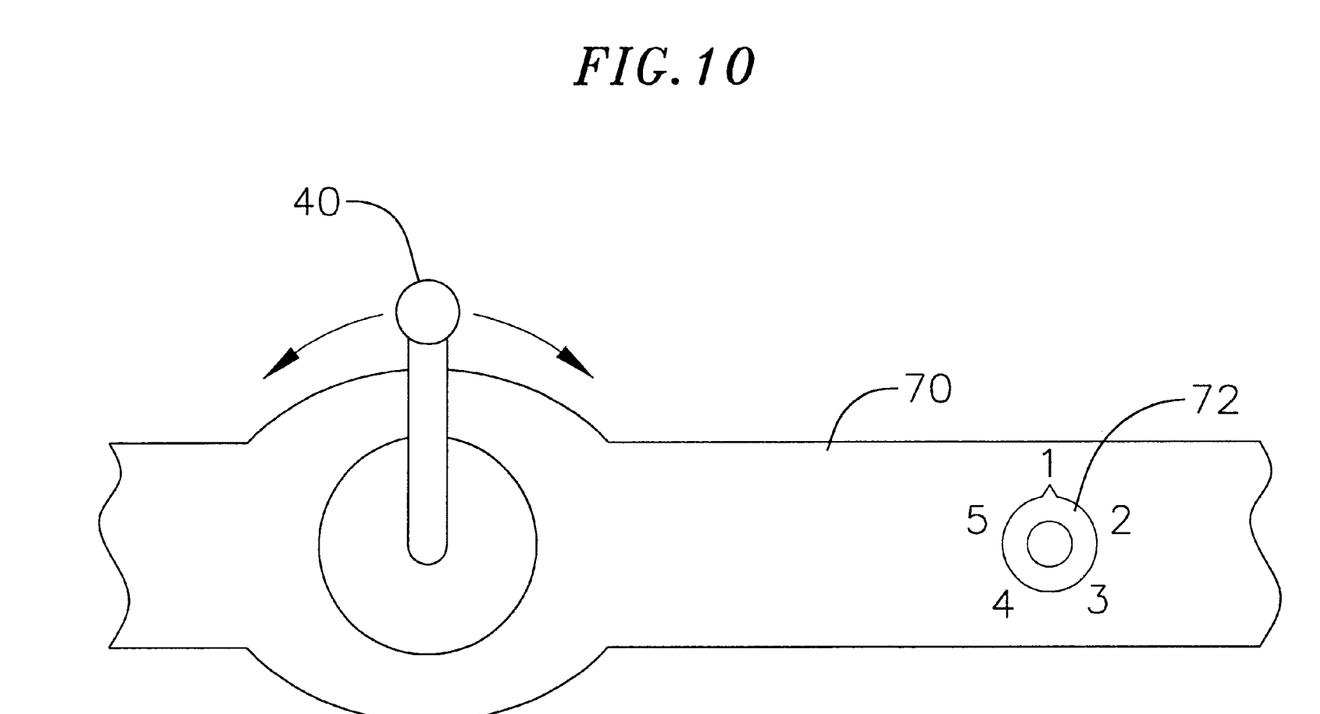
FIG. 10 is a side view of a portion of a handle in accordance with a preferred embodiment of a present invention.

The handle may also be modified as desired. The handle 70 illustrated in FIG. 10, for example, does not include the slider 54 found on handle 16. Instead, the handle 70, which is otherwise substantially identical to handle 16, includes a rotatable knob 72 that is connected to a gear and rack arrangement within the handle (not shown) that drives the stylet. A suitable gear and rack arrangement is disclosed in U.S. Pat. No. 5,364,351, which is incorporated herein by reference.

III. Catheter-Based Probe Structures With Porous Distal Regions

Figure 11:
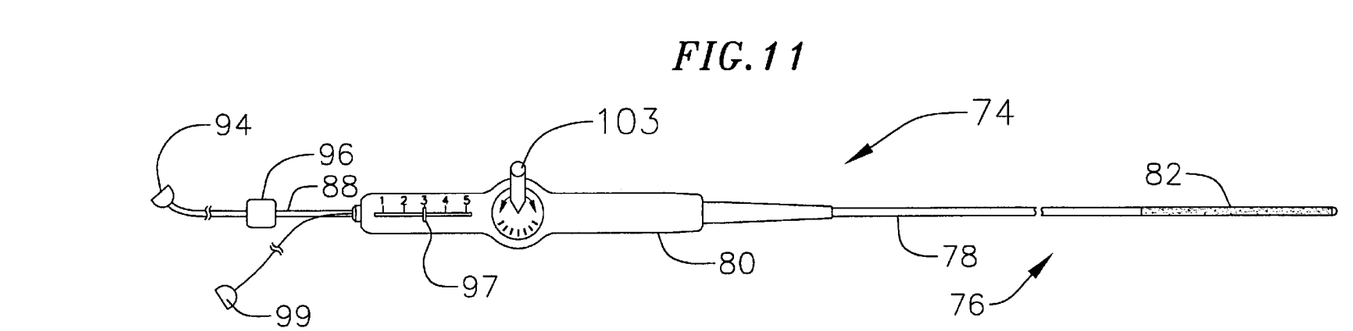
FIG. 11 is a side view of a probe in accordance with a preferred embodiment of a present invention.
Figure 12:
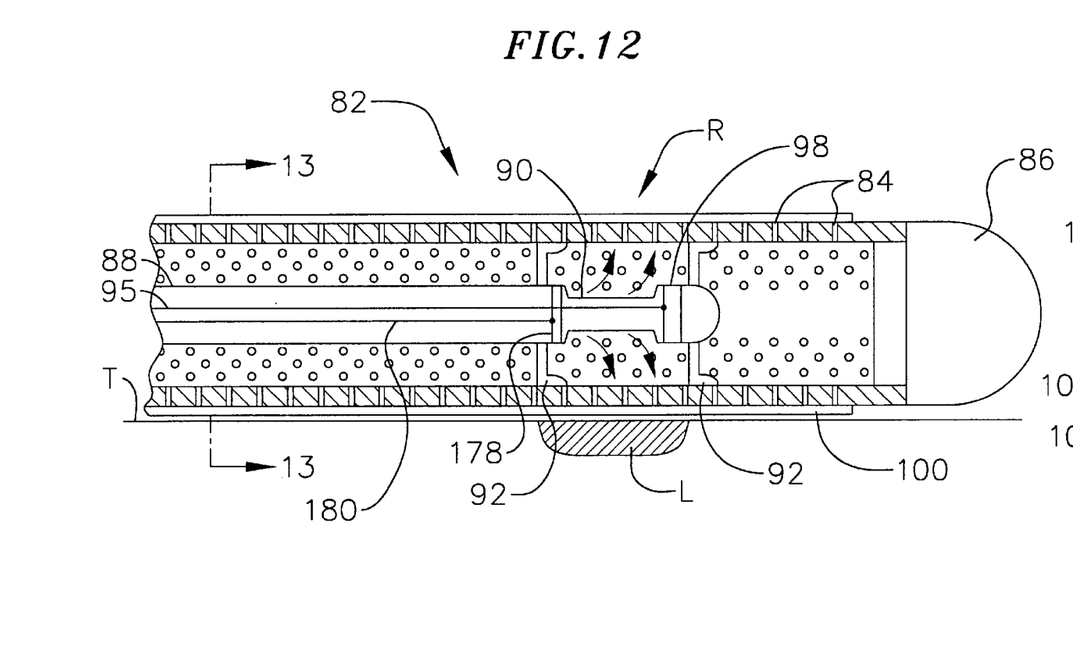
FIG. 12 is a side, partial section view of the distal portion of the probe illustrated in FIG. 11.
Figure 13:
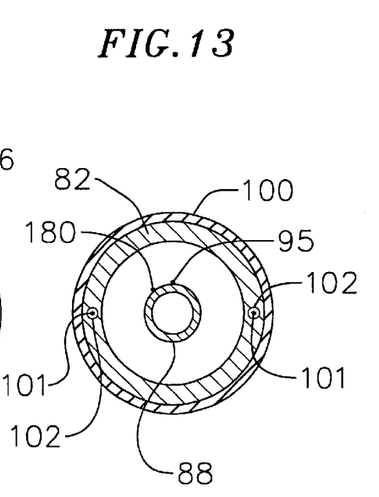
FIG. 13 is a section view taken along line 13—13 in FIG. 12.

Turning to FIGS. 11–13, the present inventions also have application in probes that employ conductive fluid to transmit energy to tissue. The exemplary catheter 74 illustrated in FIGS. 11–13 includes a hollow, flexible catheter body 76 that is preferably formed from two tubular parts, or members, both of which are non-conductive. The proximal member 78 is relatively long and is attached to a handle 80, while the distal member 82, which is relatively short, includes a plurality of small apertures 84. The proximal member 78 is typically formed from a biocompatible thermoplastic material, such as a Pebax® material and stainless steel braid composite. The distal member 82 is typically formed from a softer, more flexible biocompatible thermoplastic material such as unbraided Pebax® material, polyethylene, or polyurethane. The small apertures 84 typically range from about 0.02 micron to about 0.4 micron in diameter, but are functional in smaller sizes provided that the material is permeable and hydrophilic. Alternatively, 0.002 inch to 0.012 inch apertures with saline infusion to the outside of the distal member 82 may also be employed.

The proximal and distal members, which are about 5 French to about 9 French in diameter, are preferably either bonded together with an overlapping thermal bond or adhesively bonded together end to end over a sleeve in what is referred to as a "butt bond." The distal end of the distal member 82 is sealed with a metal or plastic tip member 86 that is secured to the distal member with adhesive.

Fluid is supplied to portions of the distal member 82 through a slidable lumen 88 that may be formed from Pebax® or other suitable non-conducive material. The distal region of the slidable lumen 88 includes a pair of fluid apertures 90 and a pair of gaskets 92. Fluid flowing through the apertures 90 is restricted to the region between the gaskets 92, thereby defining a movable lesion formation region R. A small protrusion or other stop member (not shown) may be provided near the distal end of the proximal member 78 to prevent the distal portion of the lumen 88 and the gaskets 92 from being moved out of the distal member 82.

The proximal portion of the slidable lumen 88 extends through an aperture in the handle 80 and includes a connector 94 for connecting the lumen to a source of conductive fluid. A handle 96 is provided to make it easier for the physician to grip the proximal portion of the slidable lumen 88 and move the lesion formation region R. A slidable tab 97, which is connected to the slidable lumen 88, may be positioned on the exterior of the handle 80 adjacent to indicia representative of various portions of the distal member 82 to help the physician position the movable lesion formation region R.

An electrode 98 that supplies coagulating energy to the tissue T by way of the conductive fluid to form the lesion L is carried by the portion of slidable lumen 88 between the gaskets 92. The electrode 98 should be formed from material with both relatively high electrical conductivity and relatively high thermal conductivity. Suitable materials include gold, platinum, and platinum/iridium. Noble metals are preferred. The electrode 98 is connected to a PC board within the handle 80 by a wire 95 that is secured to the exterior of the slidable lumen 88 over much of its length. The PC board is, in turn, connected to a connector 99 in conventional fashion.

The conductive fluid preferably possesses a low resistivity to decrease ohmic loses, and thus ohmic heating effects, within the catheter. The composition of the electrically conductive fluid can vary. A hypertonic saline solution, having a sodium chloride concentration at or near saturation, which is about 20% weight by volume is preferred. Hypertonic saline solution has a low resistivity of only about 5 ohm·cm, compared to blood resistivity of about 150 ohm·cm and myocardial tissue resistivity of about 500 ohm·cm. Ionic contrast solution, which has an inherently low resistivity, can be mixed with the hypertonic saline solution. The mixture enables radiographic identification of the lesion formation region R without diminishing the ionic transfer through the pores.

The small apertures 84 are large enough for the conductive fluid to flow through. Because the flow of conductive fluid into the body is often undesirable, the exemplary embodiment illustrated in FIGS. 11–13 includes a layer of microporous material 100 that covers the distal member 82 and facilitates the transfer of energy into the tissue, while preventing most conductive fluid perfusion. The pores in the microporous layer 100 establishes ionic transport of the tissue coagulating energy from the electrode 98 through the electrically conductive fluid to tissue.

More specifically, due largely to mass concentration differentials across the pores of the microporous layer 100, ions in the conductive fluid will pass into the pores because of concentration differential-driven diffusion. Ion diffusion through the pores will continue as long as a concentration gradient is maintained across the microporous layer 100. The ions contained in the pores provide the means to conduct current across the microporous layer 100. When RF energy is conveyed from a RF power supply and control apparatus to the electrode 98, electric current is carried by the ions within the pores. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of fluid through the pores. The ions convey RF energy through the pores into tissue to a return electrode, which is typically an external patch electrode (forming a unipolar arrangement). Alternatively, the transmitted energy can pass through tissue to an adjacent electrode (forming a bipolar arrangement). The RF energy heats tissue (mostly ohmically) to coagulate the tissue and form a lesion.

With respect to materials, the exemplary microporous layer 100 illustrated in FIGS. 11–13 is preferably formed from regenerated cellulose or a microporous elastic polymer. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. The micropores should occupy about 1% of the surface area and be about 0.02 micron to about 0.4 micron in diameter, but are functional in smaller sizes provided that the material is permeable and hydrophilic. A slightly larger pore diameter may also be employed. Because the larger pore diameter would result in significant fluid transfer through the porous region, a saline solution having a sodium chloride concentration of about 0.9% weight by volume is preferred. Smaller pores may be used. However, the surface are should be increased.

The exemplary catheter 74 is also a steerable catheter and, to that end, includes a pair of steering wires 101 that extend through steering wire lumens 102 that are formed in the catheter body wall. Preferably, the catheter body proximal and distal members 78 and 82 are triple lumen extrusions. The individual lumen portions are aligned during assembly of the catheter body 76 to form the steering lumens 102. [The micropores should not be formed in the area of the steering lumens 102.] The proximal ends of the steering wires 101 are connected to a control knob 103 on the catheter handle 80 and the distal ends are anchored near the distal ends of the steering wire lumens 102. So configured, rotation of the control knob 103 causes the distal portion of the catheter to deflect. Additional information concerning the use of steering wires in a catheter body wall may be found in U.S. Pat. No. 5,676,653 and U.S. application Ser. No. 09/165,652, which is entitled "Steerable Device For Introducing Diagnostic And Therapeutic Apparatus Into The Body," both of which are incorporated herein by reference.

The exemplary catheter illustrated in FIGS. 11–13 may be used to form lesions of various length much in the same manner as the catheters described above with reference to FIGS. 1–10. More specifically, once the distal member 82 is properly positioned within the body, the physician can move the lesion formation region R (by moving the slidable lumen 88) to the desired location. The lesion formation region R is then filled with conductive fluid and power is supplied to the electrode 98 to form the first portion of the lesion. The lesion formation region R is then moved to an adjacent tissue area and power is again applied to form the next portion of the lesion. This process may be repeated until a lesion having the desired length has been formed. Alternatively, power may be continuously applied as the lesion formation region R is being moved.

IV. Imaging

On-board imaging capability, which allows the physician to monitor the formation of lesions, may also be provided in probes embodying the present inventions. The exemplary catheter 104 illustrated in FIGS. 14–16 includes such imaging capability in addition to many of the features of the catheters described above with reference to FIGS. 1–13. More specifically, exemplary catheter 104 includes a hollow, flexible catheter body 106 that is preferably formed from a proximal member 108, which is relatively long and is attached to a handle 110 and a distal member 112, which is relatively short and carries a plurality of spaced electrodes 114. The proximal member 108 is typically formed from a biocompatible thermoplastic material, such as a Pebax® or polyethylene material and stainless steel braid composite, which has good torque transmission properties, while the distal member 112 is typically formed from a softer, more flexible biocompatible thermoplastic material such as unbraided Pebax® material, polyethylene, or polyurethane. The proximal and distal members, which are about 5 French to about 9 French in diameter, are preferably either bonded together with an overlapping thermal bond or adhesively bonded together end to end over a sleeve in what is referred to as a "butt bond." Here, however, the electrodes 114 must be formed from conductive materials such as metal powder and plastic composites because pure metal electrodes would interfere with imaging.

Like the exemplary distal member 18 illustrated in FIGS. 1–4, the exemplary distal member 112 includes a pair of end sections 116 and a plurality of intermediate sections 118 positioned between adjacent electrodes 114. Each distal member section is non-conductive. The electrodes 114 may be secured to the distal member sections with adhesive or thermal bonding techniques during assembly. A tip member 119 is secured to the distal end of the catheter body 106.

Figures 14, 15, 16:
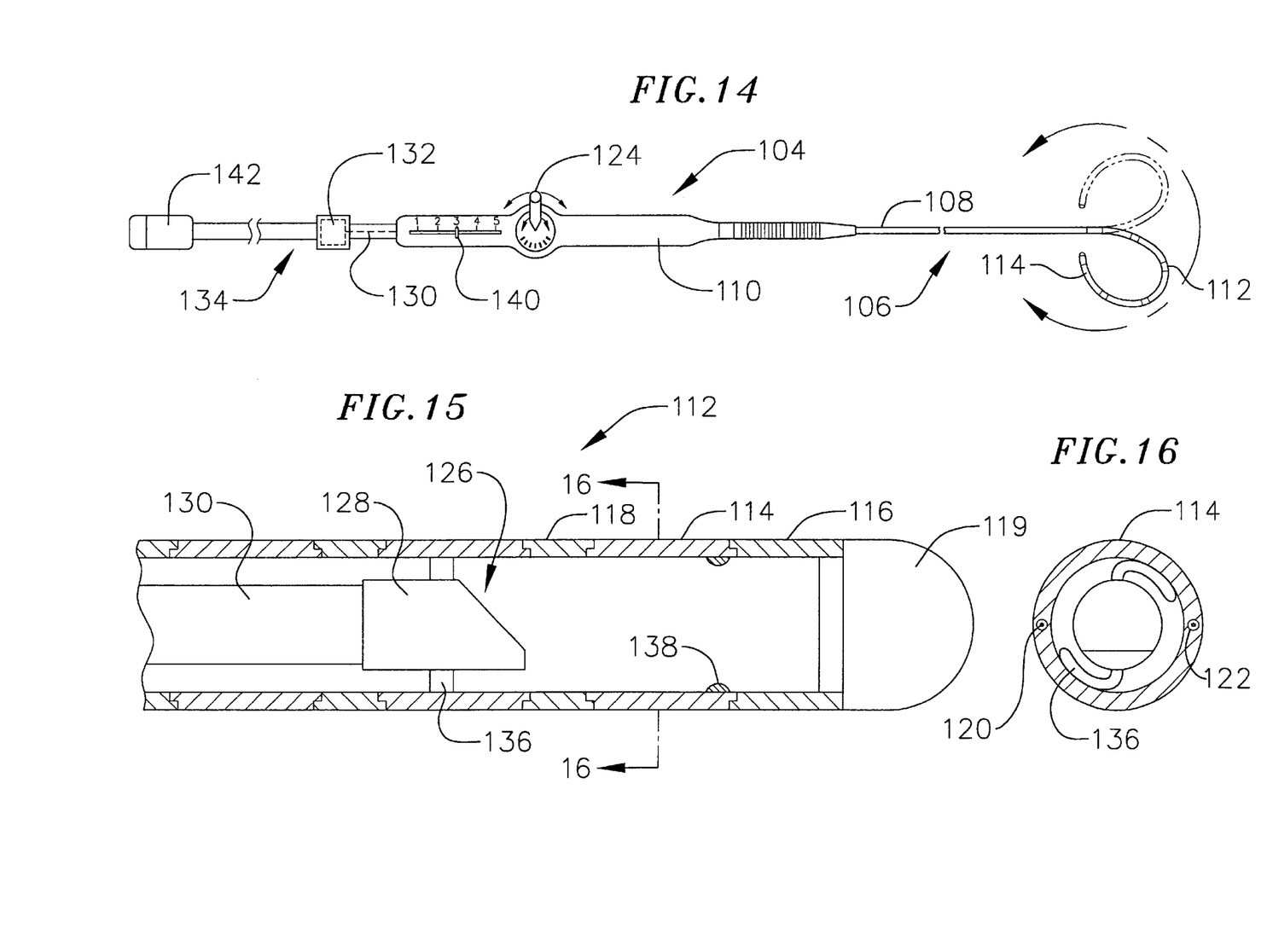
FIG. 14 is a side view of a probe in accordance with a preferred embodiment of a present invention.
FIG. 15 is a side, partial section view of the distal portion of the probe illustrated in FIG. 14.
FIG. 16 is a section view taken along line 16—16 in FIG. 15.

To facilitate bi-directional steering, the exemplary catheter 104 illustrated in FIGS. 14–16 includes a pair of steering wires 120 that extend through steering wire lumens 122. Respective portions of the steering wire lumens 122 are formed in the catheter body proximal member 108, distal member sections 116 and 118, and electrodes 114, each of which has a triple lumen design. The proximal member 108, electrodes 114, and distal member sections 116 and 118 are preferably formed as triple lumen extrusions. The individual lumen portions are aligned with one another during assembly to form the steering lumens 122. The proximal ends of the steering wires 120 are connected to a control knob 124 on the catheter handle 110 and the distal ends are anchored near the distal ends of the steering wire lumens 122. So configured, rotation of the control knob 124 causes the distal portion of the catheter 104 to deflect.

A single lumen and steering wire may, of course, be used to provide unidirectional steering.

Turning to the imaging aspects, a slidable imaging device 126 is positioned within the catheter body 106. Although not limited to such a device, the imaging device in the exemplary embodiment is an ultrasonic imaging device including a conventional ultrasonic transducer (not shown) that is located within a transducer housing 128. The transducer housing 128 is mounted on the end of a rotatable cable 130. A motor 132, which is mounted within a slidable handle 134, is used to rotate the cable 130 (and transducer housing 128) in conventional fashion. Additional details concerning the operation of ultrasonic imaging devices may be found in U.S. Pat. No. 5,131,397, which is incorporated herein by reference.

The transducer housing 128 also carries a pair of spring-like electrical contacts 136, thereby forming an actuator that may be moved from electrode to electrode by moving the slidable handle 134 to create lesions in the manner described above. The electrical contacts 136 are, as illustrated in FIG. 16, curved to facilitate rotation of the transducer housing 128. Movement of the housing 128 and electrical contacts 136, which is limited by proximal (not shown) and distal protrusions 138, may be also monitored using a slidable tab 140 that is connected to the slidable actuator handle 134 and handle indicia representative of the respective electrodes 114. [FIG. 14.] The ultrasonic transducer, motor 132 and electrical contacts 136 are connected to PC board in the handle 110 by various wires in conventional fashion (not shown), which is in turn connected to a connector 142.

Another exemplary probe, which includes both on-board imaging capability and a porous distal region, is illustrated in FIGS. 17–20 and is generally represented by reference numeral 144. Probe 144 includes many of the same elements as exemplary probe 74 (FIGS. 11–13) and exemplary probe 104 (FIGS. 14–16). The same (or similar) elements are represented by the same (or similar) reference numerals. Such common elements are discussed in detail above and, therefore, are only discussed as necessary with respect to probe 144.

Figure 17:
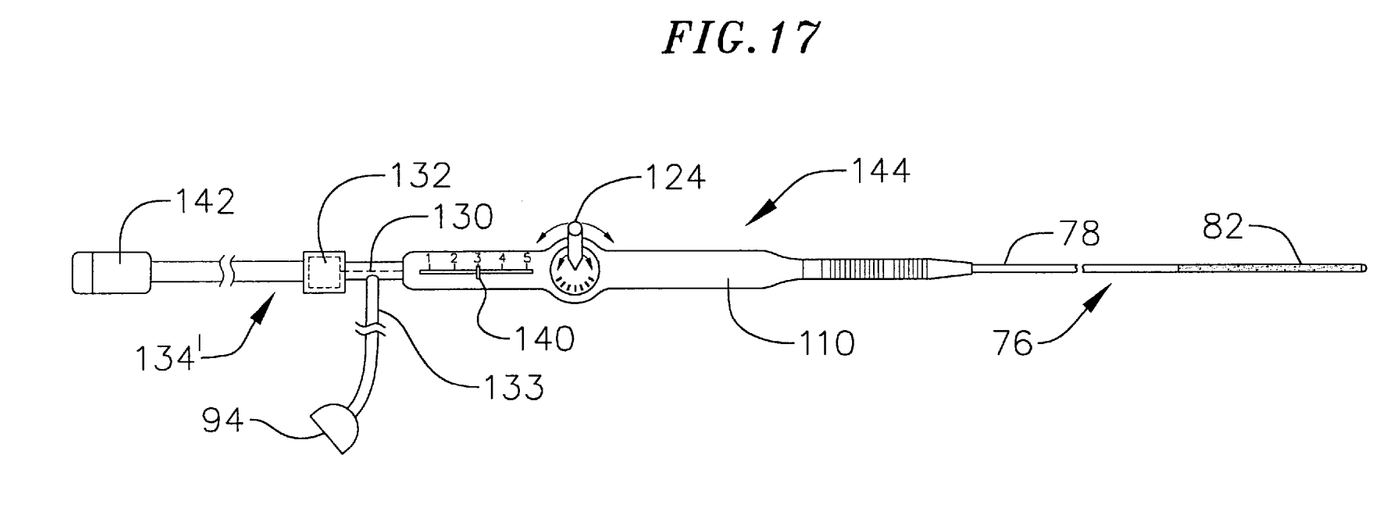
FIG. 17 is a side view of a probe in accordance with a preferred embodiment of a present invention.
Figure 18:
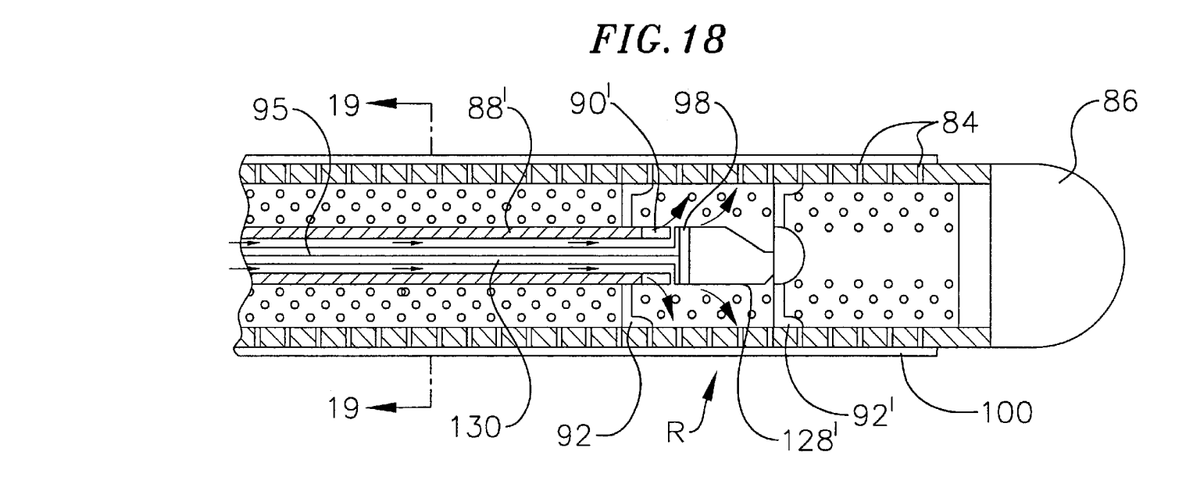
FIG. 18 is a side, partial section view of the distal portion of the probe illustrated in FIG. 17.
Figure 19:
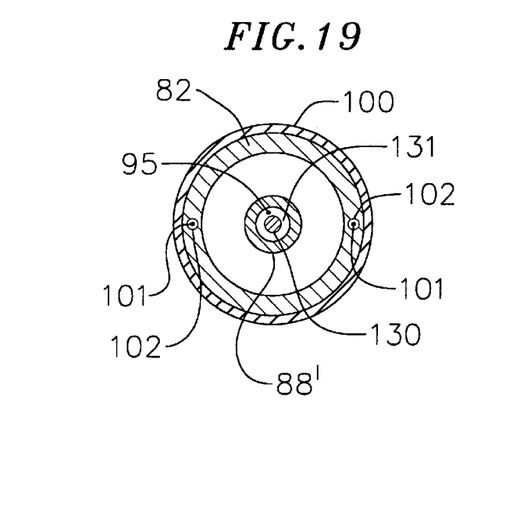
FIG. 19 is a section view taken along line 19—19 in FIG. 18.

The exemplary probe 144 includes a hollow, flexible catheter body 76 with a proximal member 78 that is relatively long and attached to a handle 110, and a distal member 82, which is relatively short and has a plurality of small apertures 84. The distal end of the distal member 82 is sealed with a metal or plastic tip member 86. Fluid is supplied to portions of the distal member 82 through a slidable lumen 88' that includes a pair of fluid apertures 90'. A pair of gaskets 92 and 92' are positioned on opposite sides of the apertures 90'. Fluid flowing through the apertures 90' is restricted to the region between the gaskets 92 and 92', thereby defining a movable lesion formation region R.

The proximal portion of the slidable lumen 88' is mounted within the slidable handle 134'. A rotatable cable 130 passes through the slidable lumen 88' and extends from a motor 132 to the housing 128' of an imaging device 126'. A fluid transmission space 131 is defined between the exterior of the cable 130 and the inner surface of the slidable lumen 88'. A suitable gasket or other sealing device (not shown) is provided at the proximal end of the slidable lumen 88' to prevent fluid leakage. Fluid is supplied to the transmission space 131 by a tube 133 that is connected to a source of conductive fluid by a connector 94. The electrode 98 that supplies coagulating energy to the tissue by way of the conductive fluid is carried by the proximal end of the transducer housing 128' and is connected to a source of energy by a wire 95. Alternatively, the electrode 98 may be mounted on the distal end of the slidable lumen 88' between the apertures 90' and the gasket 92.

Figure 20:
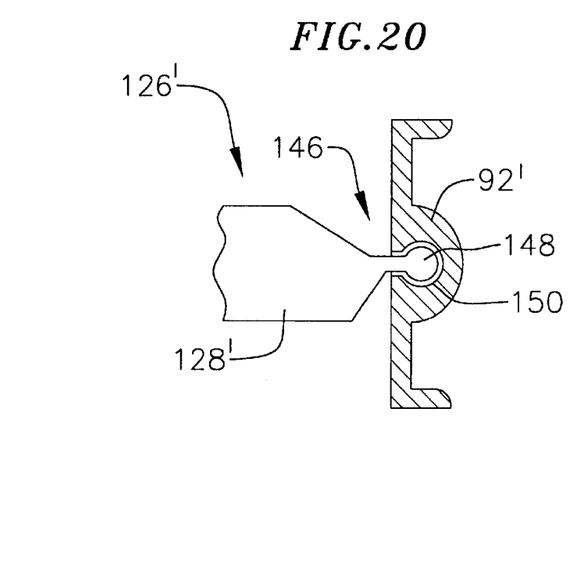
FIG. 20 is a side, partial section view of a portion of the probe illustrated in FIG. 17.

Referring more particularly to FIG. 20, the transducer housing 128' is preferably connected to the gasket 92' by a ball and socket arrangement 146 that allows the housing to rotate relative to the gasket and the slidable lumen 88'. In the illustrated embodiment, the transducer housing 128' is provided with a ball 148 that is mounted within a socket 150 formed in the gasket 92'. This arrangement may be reversed such that the housing 128' includes the socket and the gasket 92' includes the ball. Other arrangements that rotatably connect the transducer housing 128' to the gasket 92' may also be employed.

V. Surgical Probe Structures

Each of the structures described above are also adaptable for use with probes other than catheter-based probes. For example, the structures described above may also be used in the manner described above in conjunction with hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in U.S. Pat. No. 6,142,994, which is incorporated herein by reference.

Surgical probes in accordance with the present inventions preferably include a handle, a relatively short shaft, and one of the actuation devices described above in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

Figure 21:
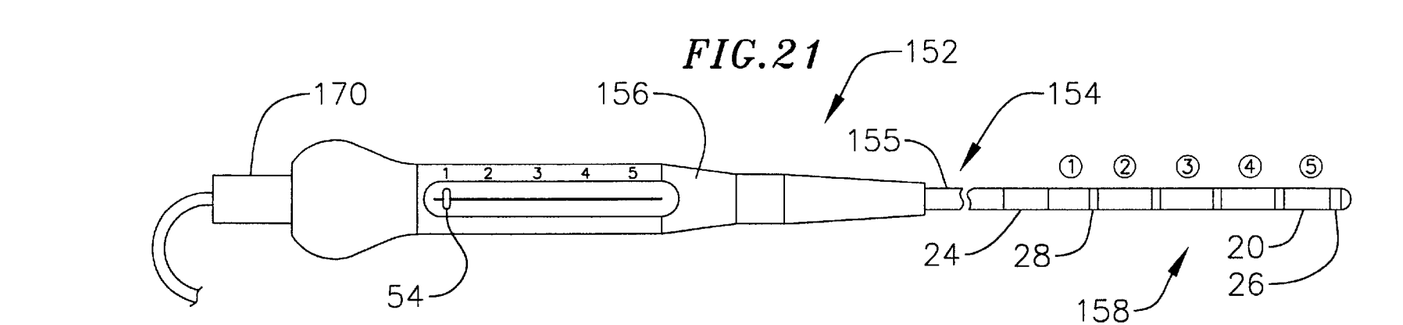
FIG. 21 is a side view of a probe in accordance with a preferred embodiment of a present invention.
Figure 22:
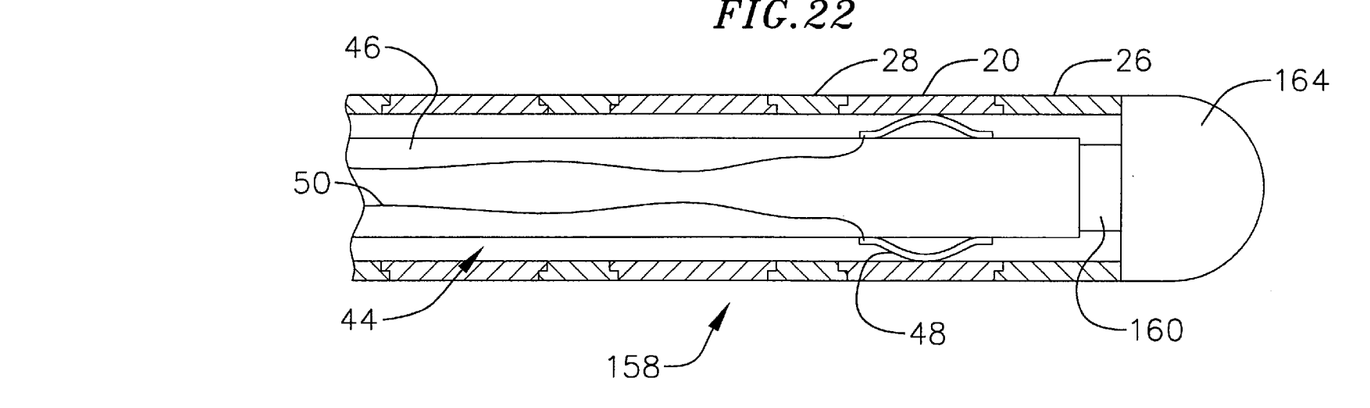
FIG. 22 is a side, partial section view of a portion of the probe illustrated in FIG. 21.
Figure 23:
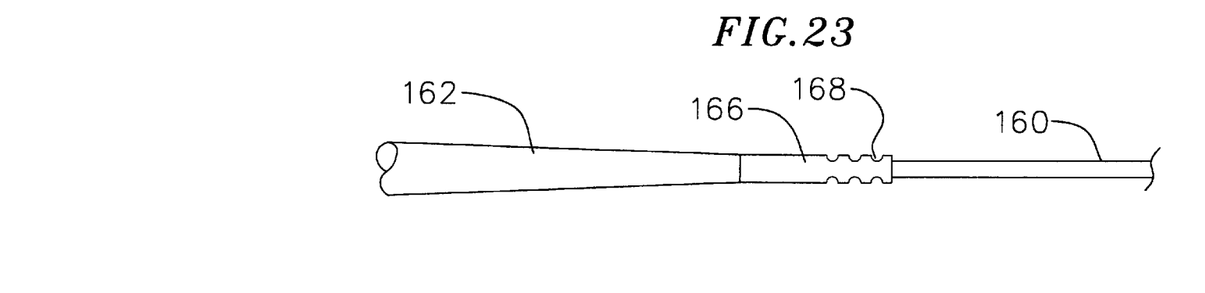
FIG. 23 a partial side view of a distal structure that may be used in conjunction with a probe such as that illustrated in FIGS. 21 and 22.

As illustrated for example in FIGS. 21–23, an exemplary surgical probe 152 includes a relatively short shaft 154, a handle 156, and a distal section 158. The shaft 154 consists of an outer polymer tube 155 and a hypo-tube (not shown), which is either rigid or relatively stiff (preferably malleable), positioned within the outer tube such that a small space is defined therebetween. The exterior of the distal section 158 is essentially identical to the exterior of the distal member 18 described above with reference to FIGS. 1–3 and the same elements are represented by the same reference numerals in FIGS. 21 and 22. More specifically, the exemplary distal section 158 includes a pair of nonconductive end sections 24 and 26 and a plurality of non-conductive intermediate sections 28 positioned between adjacent conductive electrodes 20. The end section 24 and outer tube 155 may be either bonded together with an overlapping thermal bond or adhesively bonded together end to end over a sleeve in what is referred to as a "butt bond."

The interior of the distal section 158 preferably includes a spring member 160 and a tapered malleable member 162. The spring member 160 is secured to a tip member 164 by adhesive or welding, and the malleable member 162 is secured to the shaft hypotube by welding or other suitable methods. In a preferred implementation having five electrodes, the malleable member 162 will extend to third electrode, although this may be varied depending on the intended application. The spring member 160 and malleable member 162 may be secured to one another with a stainless steel crimp tube 166, which is soldered or otherwise bonded to the malleable member and mechanically coupled to the spring member with crimps 168. Suitable materials for the malleable member 162 include stainless steel.

Exemplary surgical probe 152 is also provided with a selective electrode actuation arrangement similar to that illustrated in FIGS. 1–3A. Referring more specifically to FIGS. 21 and 22, the exemplary surgical probe 152 also includes a slidable actuator that allows the electrodes to be used individually as desired by the user. As discussed in detail above, the exemplary actuator 44 includes a tubular member 46 (here positioned over the spring member 160 and tapered malleable member 162) and a pair of flexible spring-like electrical contacts 48 that are mounted on the tubular member and biased against the inner surface of the non-conductive portions of the distal section 158 and the electrodes 20, depending on location. Wires 50 extend from the electrical contacts 48 to a PC board in the handle 156, where they are electrically coupled to a connector 170 that plugs into the power supply and control or mapping device. The tubular member 46 may be connected to a slider 54 on the handle 156 by a stylet (FIG. 3A) or, alternatively, the tubular member 46 may simply extend all the way into the handle.

VI. Temperature Sensing and Power Control

Figure 24:
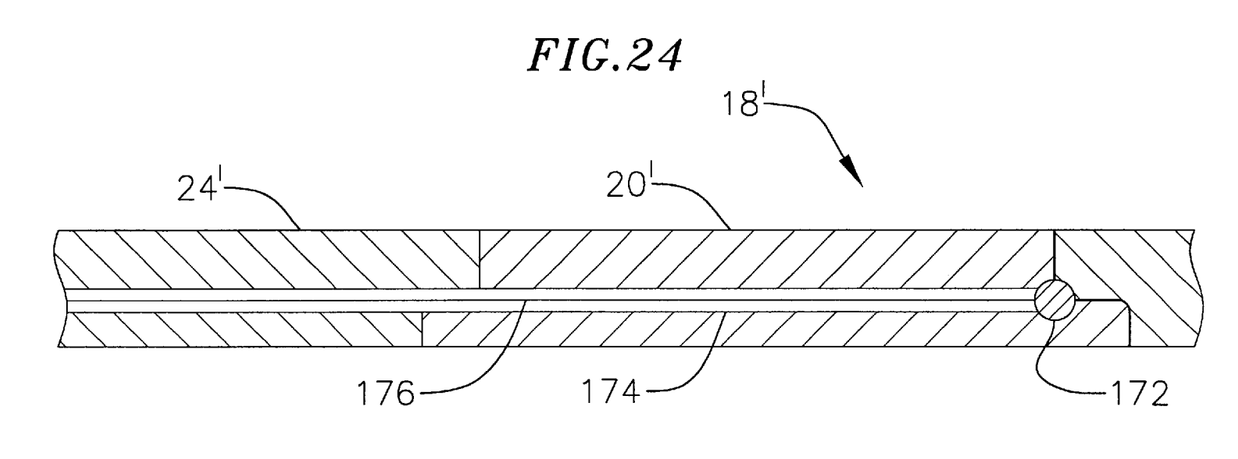
FIG. 24 is a side, section view of a temperature sensor arrangement.
Figure 25:
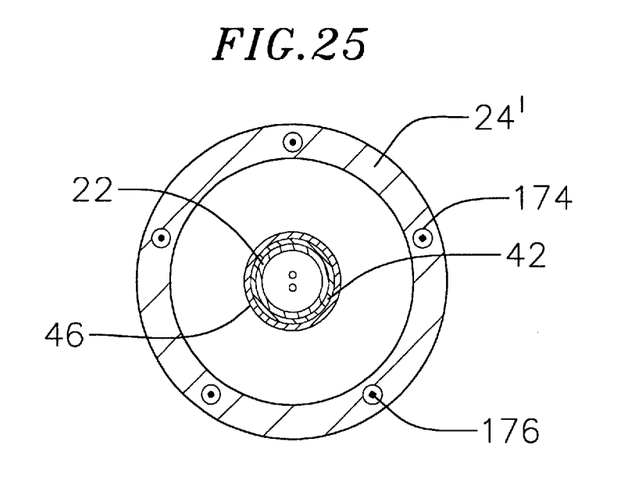
FIG. 25 is a section view of a portion of a probe including the temperature sensor arrangement illustrated in FIG. 24.

A plurality of temperature sensors, such as thermocouples or thermistors, may be located on, under, abutting the longitudinal end edges of, or in between, the electrodes. An exemplary sensing arrangement that may be used in conjunction with the devices illustrated in FIGS. 1–10, 14–16 and 21–23 is illustrated in FIGS. 24 and 25. Here, thermistors 172 may be embedded adjacent to each of the electrodes 20' during assembly. The electrodes 20', the non-conducting portions of the distal section 18', and the proximal section (not shown here) are preferably multi-lumen extrusions similar to those discussed above with reference to FIGS. 13 and 16. The lumens 174 provide passage ways for signal wires 176, which are connected to the aforementioned PC board. Suitable temperature sensors and controllers which control power to electrodes based on a sensed temperature are disclosed in U.S. Pat. Nos. 5,456,682, 5,582,609 and 5,755,715.

In those instances where conductive fluid is used, the temperature of the fluid is preferably monitored for power control purposes. To that end, a temperature sensing element, such as a thermocouple, the illustrated thermistor 178 or some other temperature sensing element (FIG. 12), may mounted on the slidable lumen 88 with the lesion formation region R. The thermocouple is connected to the aforementioned PC board in the catheter handle by a wire 180.

Although the present inventions have been described in terms of the preferred embodiments above, numerous modifications and/or additions to the above-described preferred embodiments would be readily apparent to one skilled in the art.

By way of example, but not limitation, the insulative tube 42 could be externally threaded and the tubular member 46 could have corresponding internal threads such that relative rotation would cause the tubular member to translate over the insulative tube. The structures disclosed herein may be used in conjunction with loop-type catheter-based probes such as those disclosed in U.S. Pat. No. 6,071,279, which is incorporated herein by reference.

It is intended that the scope of the present inventions extend to all such modifications and/or additions and that the scope of the present inventions is limited solely by the claims set forth below.

We claim:

1. An apparatus for performing a diagnostic or therapeutic operation on body tissue, comprising:
   a support structure defining a proximal region and a distal region;
   first and second longitudinally spaced conductive regions associated with the distal region of the support structure; and
   an actuation device including at least one electrical contact located within the support structure and movable between a first position where the at least one electrical contact is in electrical connection with the first conductive region and a second position where the at least one electrical contact is in electrical connection with the second conductive region.

2. An apparatus as claimed in claim 1, wherein the support structure comprises a catheter body.

3. An apparatus as claimed in claim 1, wherein the first and second longitudinally spaced conductive regions comprise electrodes.

4. An apparatus as claimed in claim 1, wherein the first and second longitudinally spaced conductive regions comprise first and second tubular electrodes and the support structure distal region comprises a tubular member between the first and second tubular electrodes.

5. An apparatus as claimed in claim 4, wherein the first and second tubular electrodes define inner surfaces, the support structure distal region defines an inner surface and the inner surfaces of the first and second tubular electrodes define respective portions of the inner surface of the support structure distal region.

6. An apparatus as claimed in claim 1, wherein the actuation device is slidable relative to the support structure.

7. An apparatus as claimed in claim 1, wherein the actuation device includes a tubular member that supports the at least one electrical contact.

8. An apparatus as claimed in claim 7 wherein the actuation device includes a stylet that extends proximally from the tubular member to the proximal region of the support structure.

9. An apparatus as claimed in claim 1, wherein the at least one electrical contact comprises a flexible electrical contact.

10. An apparatus as claimed in claim 1, wherein the at least one electrical contact comprises a brush.

11. An apparatus as claimed in claim 1, further comprising:

a steering mechanism within the support structure.

12. An apparatus as claimed in claim 1, further comprising:

a handle associated with the distal region of the support structure;

a control element carried by the handle and operatively connected to the actuation device.

13. An apparatus as claimed in claim 12, wherein the control element comprises a slider.

14. An apparatus as claimed in claim 1, further comprising:

an imaging device associated with the actuation device.

15. An apparatus as claimed in claim 1, wherein the conductive regions comprise a composite including a plastic material and metal powder.

16. An apparatus as claimed in claim 1, wherein the support structure and conductive regions include respective protrusions that combine to form lap joints.

17. An apparatus for performing a diagnostic or therapeutic operation on body tissue, comprising:

a support structure defining a proximal region and a distal region defining a distal region length;

a plurality of electrically conductive regions carried by the support structure distal region; and energy transmission means, at least a portion of which is movable within at least the distal region of the support structure, for selectively connecting an energy source to individual conductive regions.

18. An apparatus as claimed in claim 17, wherein the support structure comprises a catheter body.

19. An apparatus as claimed in claim 17, further comprising:

a steering mechanism within the support structure.

20. An apparatus as claimed in claim 17, further comprising:

a handle associated with the distal region of the support structure;

a control element carried by the handle and operatively connected to the movable portion of the energy transmission means.

21. An apparatus as claimed in claim 20, wherein the control element comprises a slider.

22. An apparatus as claimed in claim 17, further comprising:

an imaging device associated with the movable portion of the energy transmission means.

* * * * *